United States Patent [19]

Okamoto et al.

[11] 4,324,781

[45] Apr. 13, 1982

[54] PESTICIDAL AQUEOUS SUSPENSION

[75] Inventors: Yukikazu Okamoto, Ikeda; Manabu Tagami, Takarazuka, both of Japan

[73] Assignee: Sumitomo Chemical Company, Limited, Osaka, Japan

[21] Appl. No.: 74,371

[22] Filed: Sep. 10, 1979

[30] Foreign Application Priority Data

Sep. 8, 1978 [JP] Japan .................. 53/110942

[51] Int. Cl.$^3$ ............ A01N 37/00; A01N 43/08; A01N 47/10; A01N 61/02
[52] U.S. Cl. ............................ 424/78; 424/168; 424/170; 424/172; 424/285; 424/298; 424/300; 424/327
[58] Field of Search ............... 424/78, 300, 168, 170, 424/172, 285, 298, 327

[56] References Cited

U.S. PATENT DOCUMENTS

| | | | |
|---|---|---|---|
| 2,957,803 | 10/1960 | Woods | 424/168 |
| 3,184,380 | 5/1965 | Woods | 424/38 |
| 3,342,673 | 9/1967 | Haufman et al. | 424/300 |
| 3,658,959 | 4/1972 | Jaks | 424/300 |
| 4,067,990 | 1/1978 | Dulet | 424/300 |
| 4,071,617 | 1/1978 | Graves et al. | 424/78 |

FOREIGN PATENT DOCUMENTS

| | | |
|---|---|---|
| 1493069 | 7/1967 | France . |
| 46-20519 | 6/1971 | Japan . |
| 48-52918 | 7/1973 | Japan . |
| 48-38150 | 11/1973 | Japan . |
| 49-126635 | 3/1974 | Japan . |
| 50-76236 | 10/1974 | Japan . |
| 52-66633 | 6/1977 | Japan . |
| 52-128226 | 10/1977 | Japan . |
| 52-148625 | 12/1977 | Japan . |

OTHER PUBLICATIONS

Derwent Abstract 73757u/42 of NL patent 7403925 (eq. to Japanese 49/126635).
Derwent Abst. 49774w/30 of Fr. 2247976 (eq. to Japanese 76236/75).
Derwent Abst. 496386/28 of Japanese 66–633.
Derwent Abst. 74162y/42 of BE 853,579 (eq. to Japanese 128226).

*Primary Examiner*—Allen J. Robinson
*Attorney, Agent, or Firm*—Sughrue, Mion, Zinn, Macpeak and Seas

[57] ABSTRACT

A pesticidal aqueous suspension having an excellent dispersion stability, which comprises, as a pesticidally active ingredient, an N-methyl- or N-phenylcarbamate which is solid and has a solubility in water of about 10 to 10,000 ppm at room temperature, suspended in water in a finely dispersed state with a surfactant having a hydrophilelipophile balance (HLB) less than 5 and polyvinyl alcohol having a degree of hydrolysis of about 70 to 90 mol % and a degree of polymerization of about 300 to 2,600 as dispersing agents in the presence of ethylene glycol and liquid paraffin as dispersion stabilizers.

9 Claims, No Drawings

PESTICIDAL AQUEOUS SUSPENSION

BACKGROUND OF THE INVENTION

1. Field of the Invention

This invention relates to a stable pesticidal aqueous suspension of an N-methyl- or N-phenylcarbamate as a pesticidally active ingredient.

2. Description of the Prior Art

Conventional pesticidal formulations which are applied as aqueous dilutions consist of an emulsifiable concentrate, a wettable powder and a suspension (or a flowable formulation) which have their own advantages and are therefore used for different purposes. A suspension, especially an aqueous suspension, is considered more adaptable and advantageous than the other two formulations because it allows substituting water for an organic solvent. An organic solvent poses a potential harm to beneficial animals and plants and often presents safety problems in manufacture, storage, transportation and field application. An aqueous suspension allows all operations from manufacture to field application to be accomplished in a wet system, thus eliminating the disadvantages caused by the drifting of the dusty particles of the formulation, and it can be prepared at lower cost from a less expensive materials. However, the suspension is afflicted with a serious problem with retention of its physical properties that prevents its expanded use. As the formulation is stored for an extended period, its dispersed particles grow larger or separate from the dispersion medium to form sediments. It therefore would be a great contribution to the art if this problem could be solved and a stable aqueous suspension were provided.

The term "pesticidal aqueous suspension" used herein means a composition which has fine particles of a pesticidally active ingredient dispersed in water together with dispersion agents. Such composition is prepared by various conventional methods such as by using an air mill or a hammer mill to make fine particles of a solid pesticide which is then dispersed in water with a dispersing agent, or by adding a solid pesticide to a dispersion agent containing water and dispersing the pesticide by making fine particles thereof with the use of a wet grinder such as a comminutor, ball mill, oscillating mill, tower mill, attritor, colloid mill or sand mill, as is disclosed in Japanese Patent Publication No. 20519/71; or by forming a solution of the solid pesticide in a hydrophilic solvent and adding the solution into water to crystallize fine particles of the pesticide suitable for dispersion in water, as is disclosed in Japanese Patent Publication No. 38150/73.

The thus prepared suspension cannot maintain its physical properties stably over an extended period and therefore cannot be used as a commercial product without suitable treatments. Several methods have therefore been proposed to improve the stability of the physical properties of such conventional suspension; for example, controlling the specific gravity of the disperse phase or dispersion medium, or controlling the viscosity of the suspension system, or preventing formation of a layer of a hard sediment (hard cake) to assure easy re-dispersing at the time of field application. Specific examples of these conventional methods are: using finely ground particles of a petroleum resin, coumarone resin or ester gum together with a water soluble polymer to provide the mixture with suitable viscosity and thixotropic properties, thus preventing deterioration of the physical properties during storage (see Japanese Patent Publication No. 148625/77); use of colloidal silicone and other agents that assure resuspending (see Japanese Patent Publication (OPI) No. 52918/73) (the term "OPI" as used herein refers to a "published unexamined Japanese patent application"); addition of a dye of a metal complex compound to prevent crystallization of an aqueous dispersion (see Japanese Patent Application (OPI) No. 126635/74); using a concentrated aqueous solution of ammonium sulfate or sodium hydrogenphosphate to provide a stable suspension system (Japanese Patent Application (OPI) No. 76236/75); adding a water soluble polymer to provide a homogeneous suspension having a viscosity between 200 to 500 cps (see Japanese Patent Application (OPI) No. 66633/77 and U.S. Pat. No. 4,071,617); stabilization of a dispersion system by addition of a hetero polysaccharide gum (xanthane gum) as disclosed in Japanese Patent Application (OPI) No. 128226/77; and stabilization of a dispersion system by addition of urea or fats, as disclosed in U.S. Pat. Nos. 2,957,803 and 3,184,380.

Generally, the physical properties of a suspension system are deteriorated due to settling, agglomeration, and growth of dispersed particles, and the prevention of the last-mentioned phenomenon is most difficult to accomplish and this is particularly prominent when a very slightly water soluble pesticidally active ingredient is dispersed in water. A pesticidally active ingredient, especially a carbamate compound, has a solubility in water generally in the range of from several tens to several thousands ppm, and a suspension of such a very slightly soluble compound is particularly low in terms of the stability of its physical properties. While an aqueous suspension generally comprises finely dispersed particles of a size in the range of from 3 to 10 microns, the dispersed particles of such "very slightly soluble compound" gradually grow larger, sometimes to a size larger than 100 microns or even several millimeters, as the dispersion is stored at room temperature for a period of 1 to 2 years. With such big particles, the suspension system not only has its stability deteriorated but also it is substantially unsuitable for field application in respect of sprayability, effectiveness or phytotoxicity to plants.

SUMMARY OF THE INVENTION

It is therefore a primary object of this invention to provide a pesticidal aqueous suspension which, due to the absence of grown or settled particles in the suspension, is easily dispersed in an aqueous diluent even after extended storage.

It has been found that a suspension of an N-methyl- or N-phenylcarbamate as a pesticidally active ingredient which is only very slightly soluble in water and cannot be incorporated in an ordinary suspension system without its particles growing larger or losing their stability, can be rendered stable over an extended period of storage by using as the surfactant a surfactant having an HLB less than 5 and by either dispersing in water a solid pesticidally active ingredient ground to a size less than about 5 microns, preferably less than 3 microns, in the presence of suitable amounts of other essential ingredients consisting of polyvinyl alcohol, ethylene glycol, and liquid paraffin; or by using a sand mill (fast rotating bead colloid dispersing machine) or other grinder to grind and disperse a mixture of the pesticidally active ingredient and the other essential ingredients (including the surfactant) in the presence of water until the size of the particles of the pesticidally active ingredient is reduced to less than about 5 microns, preferably less than about 3 microns. The surfactant having an HLB less than 5, the polyvinyl alcohol, ethylene glycol and liquid paraffin used in this invention are readily available as commercial food additives or general industrial products. In short, this invention features the use of these four essential ingredients, and should one of them be absent, the intended object of this invention cannot be achieved.

DETAILED DESCRIPTION OF THE INVENTION

Examples of the surfactant having an HLB less than 5 include sorbitan alkylate, polyoxyethylene alkyl ester, polyethylene glycol alkyl (or alklaryl) ether, monoglyceride of fatty acids, propylene glycol alkylate, saccharose alkyl ester, polyoxyethylene-polyoxypropylene block copolymer, etc, with the sorbitan alkylate, particularly, sorbitan mono-, sesqui-, tri- or tetraoleate being preferred.

A suitable polyvinyl alcohol has a degree of hydrolysis of about 70 to 90 mol%, preferably about 78 to 82 mol%, and a degree of polymerization of about 300 to 2600, preferably about 1500 to 2600.

While there is no particular limitation on the liquid paraffin that can suitably be used in this invention, those products of commercial grade having a specific gravity of from 0.815 to 0.910 at 25° C., a viscosity of from 50 to 355 Saybolt sec/100° F. (37.8° C.), and 16 to 38 carbon atoms are suitable. Equivalent of these products are the liquid paraffin and light liquid paraffin as specified in Japanese Pharmacopoeia, or the mineral oil and light mineral oil as defined in U.S. Pharmacopoeia, National Formulary.

There is no particular limitation on the ethylene glycol to be used in this invention and any commercially available product would be suitable.

Each of the surfactant and polyvinyl alcohol is used in an amount of about 0.5 to 5.0 wt% of the pesticidal aqueous suspension, and each of the ethylene glycol and liquid paraffin is used in an amount of about 5 to 30 wt% of the composition.

Suitable N-methyl- or N-phenylcarbamate compounds for use as the pesticidally active ingredient of the present invention can be represented by the formula

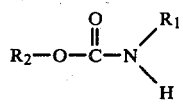

wherein $R_1$ is a methyl group, a phenyl group or a 3-chlorophenyl group; and $R_2$ is a 3-methylphenyl group, a 3,4-dimethylphenyl group, a 1-naphthyl group, a 2-methyl-2-(methylthio)propionaldehydo-oxime group, a 2,3-dihydro-2,2-dimethyl-7-benzofuranyl group, a 2-(1-methylethoxy)phenyl group, a 2-chlorophenyl group, a 2-isopropylphenyl group, a 3,5-xylyl group, a 4-dimethylamino-3,5-xylyl group or a 4-(dimethylamino)-3-methylphenyl group when $R_1$ is a methyl group, and $R_2$ is an isopropyl group when $R_1$ is a phenyl group or a 3-chlorophenyl group.

Examples of the pesticidally active ingredient are very slightly water soluble N-methyl- or N-phenylcarbamate compounds such as 3-methylphenyl N-methylcarbamate, 3,4-dimethylphenyl N-methylcarbamate, 1-naphthyl N-methylcarbamate, 2-methyl-2-(methylthio)propionaldehydo O-(N-methylcarbamoyl)oxime, 2,3-dihydro-2,2-dimethyl-7-benzofuranyl N-methylcarbamate, 2-(1-methylethoxy)phenyl N-methylcarbamate, 2-chlorophenyl N-methylcarbamate, 2-isopropylphenyl N-methylcarbamate, 3,5-xylyl N-methylcarbamate, 4-dimethylamino-3,5-xylyl N-methylcarbamate, 4-(dimethylamino)-3-methylphenyl N-methylcarbamate, isopropyl N-phenylcarbamate, isopropyl N-(3-chlorophenyl)carbamate, etc. The formulae of these carbamate compounds are set forth below in order:

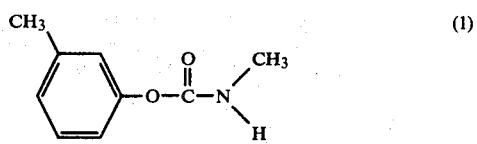

(1)

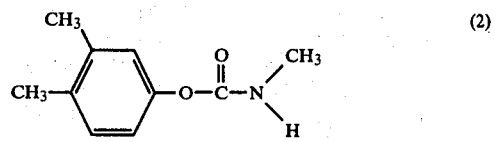

(2)

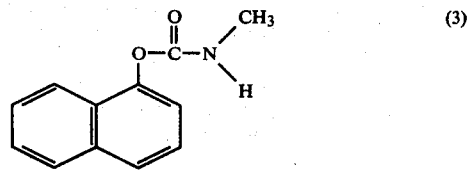

(3)

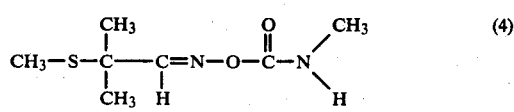

(4)

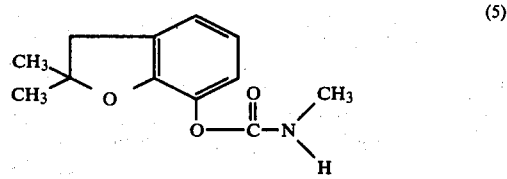

(5)

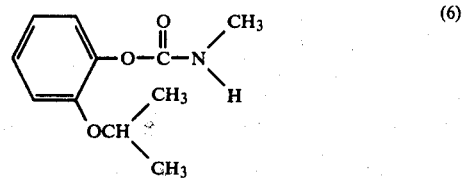

(6)

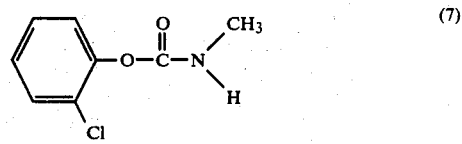

(7)

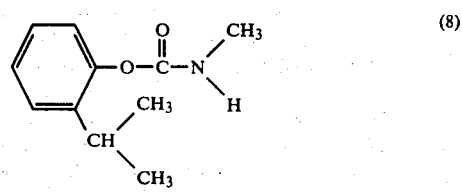

(8)

-continued

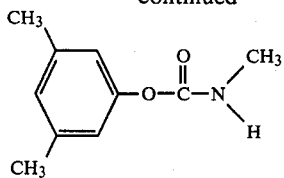 (9)

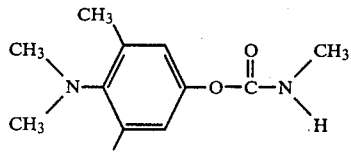 (10)

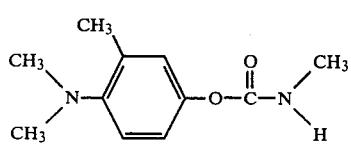 (11)

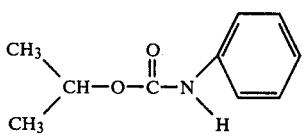 (12)

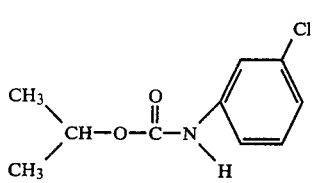 (13)

These pesticidally active ingredients are used singly or as a mixture in the pesticidal aqueous suspension of this invention in an amount in the range of about 10 to 50 wt% of the suspension. Other pesticidally active ingredients which are stable in water and which have a solubility in water within the range defined in this invention or lower solubilities may be used only if they are in combination with these carbamate compounds. These other pesticidally active ingredients may be either solid or liquid at room temperature, but it is preferred that they are contained in a smaller amount than the carbamate compounds.

It is to be understood that the pesticidal aqueous suspension of this invention contain, as required, a preservative such as O-hydroxydiphenyl, 2,4-dinitrophenol, butyl or methyl hydroxybenzoate.

The pesticidal aqueous suspension of this invention can effectively control a wide spectrum of insects which include vectors such as houseflies and mosquitoes; harmful insects in paddy fields such as rice stem borers (*Chilo suppressalis* WALKER), green rice leafhoppers (*Nephotettix cincticeps* UHLER), planthoppers like small brown planthoppers (*Laodelphax striatellus* FALLÉN) and brown planthoppers (*Nilaparvata leugen* STÅL), bugs, rice leaf beetles (*Oulema oryzae* KUWAYAMA), rice leaf miners (*Agromyza oryzae* MUNAKATA), grass leaf rollers (*Cnaphalocrocis medinalis* GUÉNÉE), rice plant skippers (*Parnara guttata* BREMER et GREY), and weevils; harmful insects in upland fields such as tobacco cutworms (*Spodoptera litura* FABRICIUS), diamondback moths (*Plutella maculipennis* CURTIS), cabbage worms, aphids and cutworms; insects harmful to fruit trees such as tortorixes, mites and fruit moths; insects harmful to trees in wood or forest such as fall webworms (*Hyphantria cunea* DRURY), gypsy moths (*Lymantria dispar* LINNÉ), and beetles; and insects harmful to stored cereals such as rice weevils (*Sitophilus zeamais* MOTSCHULSKY) and indian meal moths (*Plodenia interpunctella* HÜBNER). The composition is particularly effective against green rice leafhoppers, small brown planthoppers and brown planthoppers.

The pesticidal aqueous suspension of this invention can easily be prepared by conventional means using an apparatus generally employed by those skilled in the art. A solid pesticidally active ingredient is dry ground by a hammer mill or jet mill and the resulting particles are mixed under stirring with an aqueous mixture of a surfactant having an HLB less than 5, ethylene glycol, liquid paraffin and polyvinyl alcohol, and finally the mixture is homogenized using a homogenizer to provide a uniform suspension. Alternatively, a solid pesticidally active ingredient is mixed with an aqueous mixture of a surfactant having an HLB less than 5, ethylene glycol, liquid paraffin and polyvinyl alcohol, and the mixture is coarsely ground with a ball mill or colloid mill or other suitable device to obtain particles of the solid pesticidally active ingredient of a size substantially less than 100 microns, and then the coarse particles of the active ingredient are finely ground with a sand mill to reduce their size to less than about 5 microns, preferably less than about 2 to 3 microns, as observed under a microscope. While various materials may be used as a grinding medium for the sand mill, glass beads are most economical and therefore preferred. A suitable size of the glass beads is in the range of from 0.5 to 1.5 mm, with the narrowest size distribution being preferred. Sand milling conditions such as the amount of the grinding medium, the shape and rpm of the agitator, the viscosity of slurry and grinding time (feed rate), and their optimum levels should be determined for each pesticidal formulation in a manner well known in the art. While wet grinders other than a sand mill, such as a comminutor, ball mill or attritor, may be used, they are not so effective as the sand mill because these wet grinders provide particles whose size is distributed over a wide range or it takes a longer grinding time.

This invention will hereunder be described in greater detail by reference to the following Examples which are given here for illustrative purposes only and are by no means intended to limit the scope of this invention.

Unless otherwise indicated, all parts, percents and the like are by weight in the following examples.

EXAMPLE 1

A Shinagawa All-Purpose Mixer (a mixer manufactured by San-Ei Seisakusho, Ltd.) was used to provide a mixture of 25 parts of 3-methylphenyl N-methylcarbamate (soluble in water in 2600 ppm at 30° C.), 3 parts of sorbitan trioleate (HLB 1.8), 2 parts of Gohsenol KH-20 (polyvinyl alcohol manufactured by The Nippon Synthetic Chemical Industry Co., Ltd. having an average degree of polymerization of 2000 and a degree of hydrolysis of from 78.5 to 81.5 mol%), 15 parts of ethylene glycol, 15 parts of liquid paraffin (reagent liquid paraffin according to JIS K9003; specific gravity: 0.884, viscosity: 77.7 cSt) and 20 parts of water. A T.K. Micolloidor (manufactured by Tokushu Kika Koguo Co., Ltd.) was used to preliminarily reduce the 3-methylphenyl N-methylcarbamate to a size less than about 100 microns.

The mixture was combined with additional 20 parts of water and placed in a sand grinder (a sand mill manufactured by Igarashi Seisakusho, Ltd.) having a vessel capacity of 2 liters and filled with 1.5 liters of 1.0 to 1.5 mm glass beads, which was operated at a flow rate of 30 liter/hr with the agitator rotating at 2000 rpm to provide an aqueous suspension containing 25% fine particles of 3-methylphenyl N-methylcarbamate. The suspension was a highly flowable formulation wherein the particles of the suspended active ingredient were less than about 3 microns in size, with most of the particles having a size of about 1 micron. A 500 ml sample of the suspension was placed in a polyethylene bottle which was hermetically closed with a stopper and stored at room temperature for a period of 2 years. Neither separation of the active ingredient nor formation of a hard cake was observed. The dispersed particles of the active ingredient increased their size to only less than about 5 microns, with a center size between 1 to 2 microns. Thus, the suspension retained its high flowability as well as satisfactory physical properties. A 0.5 g sample of the suspension was metered and placed in a 250 ml measuring cylinder with a stopper. After 3° C. hard water was added to make 250 ml, the cylinder was turned upside down 30 times for thorough mixing to provide a dilution having uniformly dispersed particles of the active ingredient. The dilution was allowed to stand at 20° C. for a period of 15 minutes, and a 25 ml sample at the central portion was extracted with CHCl$_3$ and subjected to gas chromatography for measuring the active ingredient content. The following formula was used to determine the suspensibility of the active ingredient which was found to be 98.2%, suggesting the stability of the suspension system in the dilution.

Suspensibility (%) = $\frac{A.I.* \text{ in 25 ml sample (mg)} \times 10}{\text{total } A.I.* \text{ added}}$ × 100

*:Active Ingredient

COMPARATIVE EXAMPLES 1 TO 11

The procedure of Example 1 was repeated to provide pesticidal aqueous suspensions which contained the same pesticidally active ingredient and water as in Example 1 but using the surfactant having an HLB higher than 5 shown in the table with one of polyvinyl alcohol (Ingredient A), ethylene glycol (Ingredient B) and liquid paraffin (Ingredient C) being absent or replaced by a different compound. These controls were compared with the suspension of Example 1 for the presence of phase separation and growth of suspended particles. The pesticidally active ingredient, 3-methylphenyl N-methylcarbamate, was used in the same amount as in Example 1. Each of ingredients A, B and C was used in the same amount as in the respective polyvinyl alcohol, ethylene glycol and liquid paraffin in Example 1.

| Run No. | Surfactant (HLB) | Ingredient A | Ingredient B | Ingredient C |
|---|---|---|---|---|
| C-1 | Calcium lignin sulfonate (—) | polyvinyl alcohol* | ethylene glycol* | liquid paraffin* |
| C-2 | Polyoxyethylene-nonylphenol ether (12.4) | polyvinyl alcohol* | " | " |
| C-3 | Sorbitan monolaurate (7.9) | polyvinyl alcohol | " | " |
| C-4 | Sorbitan trioleate* (1.8) | none | " | " |
| C-5 | Sorbitan trioleate* (1.8) | carboxymethyl cellulose | " | " |
| C-6 | Sorbitan trioleate* (1.8) | gum arabic | " | " |
| C-7 | Sorbitan trioleate (1.8) | polyvinyl alcohol* | none | " |
| C-8 | Sorbitan trioleate* (1.8) | polyvinyl alcohol* | glycerin | " |
| C-9 | Sorbitan trioleate* (1.8) | polyvinyl alcohol* | ethylene glycol* | none |
| C-10 | Sorbitan trioleate* (1.8) | polyvinyl alcohol* | " | kerosine |
| C-11 | Sorbitan trioleate* (1.8) | polyvinyl alcohol* | " | cottonseed oil |

*the same ingredient used in Example 1.

(B) Test results

Storage conditions: 100 ml stoppered polyethylene bottle stored at 25° C. (±3° C.) for 3 months.

| | Particle Size | | Phase Separation | |
|---|---|---|---|---|
| Run No. | when prepared | after storage | upper transparent layer | hard cake |
| Ex. 1 | 3μ > | 3μ > | 0% | 0% |
| C-1 | 5μ > | 50–100μ < | 30% | 50% |
| C-2 | 5μ > | 10–50μ | 20% | 5% |
| C-3 | 3μ > | 5–30μ | 5% | 0% |
| C-4 | no dispersion formed | | | |
| C-5 | 5μ > | 5–30μ | 10% | 10% |
| C-6 | 3μ > | 10–50μ | 15% | 5% |
| C-7 | 3μ > | 50–100μ | 20% | 5% |
| C-8 | 5μ > | 10–30μ | 20% | 10% |
| C-9 | 3μ > | 50–100μ | 30% | 20% |
| C-10 | 3μ > | 10–50μ | 10% | 10% |
| C-11 | 3μ > | 10–100μ | 5% | 5% |

The above results illustrate the stability of the composition of this invention is markedly high.

EXAMPLE 2

A mixture of 20 parts of 3,4-dimethylphenyl N-methylcarbamate (soluble in water in 1300 ppm at 30° C.), 3 parts of Pluronic L-122 (the trade name of a surfactant comprising polyoxyethylene-polyoxypropylene block copolymer manufactured by Wyandotte Chemical Corp.; HLB 4), 1.5 parts of Gohsenol KH-20, 20 parts of ethylene glycol, 10 parts of liquid paraffin (JIS No. 4, a viscosity between 32 and 39 cSt) and 45.5 parts of water was subjected to the same treatment as Example 1 to thereby provide a pesticidal aqueous suspension. The suspension contained dispersed particles of the carbamate of a size less than about 3 microns. The suspension was placed in a 500 ml polyethylene bottle, airtightly closed with a stopper, and stored at room temperature for a period of 2 years as in Example 1. Neither phase separation nor formation of a hard cake was observed. The dispersed particles of the carbamate increased in size to only less than about 5 microns.

EXAMPLE 3

40 parts of 1-naphthyl N-methylcarbamate dry ground by a Jet-O-mizer (a jet mill manufactured by Seishin Kigyo K.K.) were mixed with a Shinagawa All-Purpose Mixer together with 2 parts of sorbitan trioleate (HLB 1.8), 1 part of Gohsenol KH-17 (polyvinyl alcohol having a degree of hydrolysis of from 78.5 to 81.5 mol% and an average degree of polymerization of 1700), 10 parts of ethylene glycol, 10 parts of CARNATION (trademark for liquid paraffin manufactured by Witco Chemical Company, Inc.; a viscosity between 65 and 75 Saybolt sec/100° F., a specific gravity between 0.835 and 0.845) and 37 parts of water. The mixture was further homogenized by an AUTO HOMO-MIXER (a homogenizer manufactured by Tokushu Kika Koguo Co., Ltd.) to provide a pesticidal aqueous suspension. The suspension was stored at room temperature for a period of 2 years in the same manner as Example 1. Neither phase separation nor formation of a hard cake was observed. The dispersed particles of the carbamate little increased their size.

EXPERIMENT 1

Each of pesticidal aqueous suspensions prepared in Examples 1, 2 and 3 were placed in a glass bottle which was stoppered and stored at room temperature for a period of one year as well as at 40° C. for a period of 3 months. As the table below shows, each of the carbamates incorporated in the suspensions suffered little degradation and therefore remained practically effective after storage.

| Test Sample | Carbamate Content (%) (Residual carbamate in parentheses) | | |
|---|---|---|---|
| | when prepared | 40° C., 3 mos. | Room Temp. 1 yr. |
| 3-methylphenyl N-methylcarbamate (Ex. 1) | 24.3 | 23.4 (96.3) | 23.6 (97.1) |
| 3,4-dimethylphenyl N-methylcarbamate (Ex. 2) | 20.1 | 19.5 (97.0) | 19.7 (98.0) |
| α-naphthyl N-methylcarbamate (Ex. 3) | 39.8 | 38.5 (96.7) | 39.5 (99.2) |

EXAMPLE 4

The procedure of Example 1 was repeated except that the pesticidally active ingredient was 25 parts of 2-methyl-2-(methylthio)propionaldehydo O-(N-methylcarbamoyl)oxime (soluble in water in 6000 ppm at 25° C.). A highly flowable pesticidal aqueous suspension was produced which contained dispersed particles of the carbamate less than 3 microns in size. 100 ml of the suspension was placed in a polyethylene bottle which was stoppered and stored for a period of 3 months both at room temperature and at 40° C. The dispersed particles of the carbamate increased in size to only less than 5 microns. 0.5 g of the suspension was then placed in a 250 ml measuring cylinder with a stopper and suspendability of the carbamate was determined in the same manner as Example 1. The results were 95.2% for the sample stored at room temperature, and 90.5% for the sample stored at 40° C. Hence, in a dilution of the suspension the carbamate articles were stably dispersed.

EXAMPLE 5

A mixture of 30 parts of 2,3-dihydro-2,2-dimethyl-7-benzofuranyl N-methylcarbamate (soluble in water in 700 ppm at 25° C.), 3 parts of sorbitan trioleate, 2 parts of Gohsenol KH-20, 15 parts of ethylene glycol, 10 parts of CARNATION (the trademark for liquid paraffin manufactured by Witco Chemical Company, Inc.; a viscosity between 65 and 75 Saybolt sec./100° F., a specific gravity between 0.835 and 0.845), and 40 parts of water was treated in the same manner as Example 1 to thereby produce a highly flowable pesticidal aqueous suspension containing dispersed particles of the carbamate of a size less than 3 microns. When the suspension was stored in the same manner as Example 2, the dispersed carbamate particles experienced little growth in size, and the dispersibility of the particles upon dilution with water changed little from that when the suspension was prepared.

EXAMPLE 6

The procedure of Example 5 was repeated except that the pesticidally active ingredient was 2-(1-methylethoxy)phenyl N-methylcarbamate (soluble in water in 230 ppm at 25° C.). A highly flowable pesticidal aqueous suspension containing 40% of the carbamate was obtained. The particles of the carbamate were less than 3 microns in size. After treatment in the same manner as Example 4, no substantial change was observed in the particle size and dispersibility upon dilution with water.

EXPERIMENT 2

The suspensions prepared in Examples 1, 2, 3 and 6 were compared with controls comprising commercial emulsions of the respective pesticidally active ingredients for their effectiveness against green rice leafhoppers (*Nephotettix cincticeps* UHLER).

To ten stems of rice plant (kind: Kinnan-fu, height: 10 cm) cultivated in a 1/5,000 are Wagner pot and placed on a turntable were applied each emulsified test sample with a predetermined concentration.

After drying in air, the treated rice plants were covered with a net cage (11 cm in dia. and 40 cm ht.) in which twenty adult green rice leafhoppers (♀ 10, ♂ 10) were released per district and observed for their mortality as the 24th hour. The results are shown in Table 1 below where A.I. stands for Active Ingredient.

TABLE 1

| Run No. | A.I. (Content of A.I.) | Mortality (%) Concentration | |
|---|---|---|---|
| | | 300 ppm | 150 ppm |
| Ex. 1 | 3-methylphenyl N-methylcarbamate (25 wt %) | 100.0 | 73.3 |
| Ex. 2 | 3,4-dimethylphenyl N-methylcarbamate (20 wt %) | 100.0 | 70.0 |
| Ex. 3 | 1-naphthyl N-methylcarbamate 40 wt % | 98.3 | 71.7 |
| Ex. 6 | 2-(1-methylethoxy)phenyl N-methylcarbamate (30 wt %) | 100.0 | 65.0 |
| Con. 1* | 3-methylphenyl N-methyl- | | |

TABLE 1-continued

| Run No. | A.I. (Content of A.I.) | Mortality (%) Concentration | |
|---|---|---|---|
| | | 300 ppm | 150 ppm |
| | carbamate (30 wt %) | 100.0 | 73.3 |
| Con. 2* | 3,4-dimethylphenyl N-methylcarbamate (30 wt %) | 100.0 | 68.3 |
| Con. 3* | 1-naphthyl N-methylcarbamate (15 wt %) | 100.0 | 75.0 |
| Con. 4* | 2-(1-methylethoxy)phenyl N-methylcarbamate (25 wt %) | 96.7 | 60.0 |
| | No treatment | — | — 5.0 |

*Commercially available emulsions

The flowable formulations of this invention proved as effective as the conventional emulsifiable concentrates both at the practical concentration and at the low concentration.

EXAMPLE 7

A mixture comprising 15 parts of 3,4-dimethylphenyl N-methylcarbamate (soluble in water in 1300 ppm at 30° C.), 15 parts of 4,5,6,7-tetrachlorophthalide (soluble in water in 1–2 ppm at 25° C.), both being a pesticidally active ingredient, 2 parts of Gohsenol KH-17 (polyvinyl alcohol having a degree of hydrolysis between 78.5 to 81.5 mol%, and a degree of polymerization of 1700), 3 parts of glyceryl monooleate (HLB 3.4), 10 parts of ethylene glycol, 10 parts of JIS No. 4 liquid paraffin and 25 parts of water were coarsely ground in the same manner as Example 1, and the mixture was combined with additional 20 parts of water and finely ground in the same manner as Example 1 to thereby provide a highly flowable aqueous suspension containing dispersed particles of the pesticidally active ingredients of a size less than 3 microns. A 100 ml sample of the suspension was placed in each of two polyethylene cellophane laminated bags, one of which was heat sealed and stored at room temperature for a period of one year, and the other at 40° C. for a period of 3 months. The suspension in either bag was substantially free from phase separation, and the dispersed particles of the active ingredients increased their size to only less than 5 microns. The bag stored at room temperature for one year was opened to transfer the suspension into another container. The bag was washed with an equal volume of water and the washing was combined with the suspension, mixed thoroughly, and an additional amount of water was put into the container to make 10-fold and 300-fold dilutions which had the particles of the active ingredients uniformly dispersed therein. A 250 ml sample of each dilution was placed in a 250 ml measuring cylinder with a ground stopper, the cylinder was turned upside down 30 times for thorough mixing, and allowed to stand at 20° C. for a period of 15 minutes. A 25 ml sample of the suspension at the central portion was used to determine the suspendability of the dispersed particles of the active ingredients, which was found to be 93.2% for the 10-fold dilution and 94.3% for the 300-fold dilution. Hence, the dispersed particles of the active ingredients in the pesticidal aqueous suspension of this invention were stable even when the suspension was diluted with water.

EXAMPLE 8

A mixture of 15 parts of 3-methylphenyl N-methylcarbamate (soluble in water in 2600 ppm at 30° C.) and 15 parts of O-ethyl-O-(4-cyanophenyl)-phenylphosphorothioate (soluble in water in 0.6 ppm at 30° C.), both being a pesticidally active ingredient, 2 parts of Gohsenol KH-20, 3 parts of sorbitan trioleate (HLB 1.8), 10 parts of ethylene glycol, 45 parts of JIS No. 4 liquid paraffin and 45 parts of water was treated in the same manner as Example 7 to provide a flowable pesticidal aqueous suspension which contained dispersed particles of the active ingredients of a size less than 3 microns.

While the invention has been described in detail and with reference to specific embodiments thereof, it will be apparent to one skilled in the art that various changes and modifications can be made therein without departing from the spirit and scope thereof.

What is claimed is:

1. A pesticidal aqueous suspension having excellent dispersion stability, which comprises, based on the total weight of the suspension, (a) as a pesticidally active ingredient, about 10 to 50 wt% of an N-methyl- or N-phenylcarbamate which is solid and has a solubility in water of 10 to 10,000 ppm at room temperature suspended in water in a finely dispersed state; (b) about 0.5 to 5 wt% surfactant having a hydrophile-lipophile balance (HLB) less than 5; (c) about 0.5 to 5 wt% polyvinyl alcohol having a degree of hydrolysis of about 70 to 90 mol% and a degree of polymerization of about 300 to 2,600; (d) about 5 to 30 wt% ethylene glycol; and (e) about 5 to 30 wt% liquid paraffin.

2. The pesticidal aqueous suspension of claim 1, wherein said N-methyl- or N-phenylcarbamate is represented by the formula:

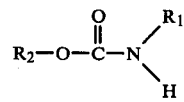

wherein $R_1$ is a methyl group, a phenyl group or a 3-chlorophenyl group; $R_2$ is a 3-methylphenyl group, a 3,4-dimethylphenyl group, a 1-naphthyl group, a 2-methyl-2-(methylthio)propionaldehydo-oxime group, 2,3-dihydro-2,2-dimethyl-7-benzofuranyl group, a 2-(1-methylethoxy)phenyl group, a 2-chlorophenyl group, a 2-isopropylphenyl group, a 3,5-xylyl group, a 4-dimethylamino-3,5-xylyl group, or a 4-(dimethylamino)-3-methylphenyl group when $R_1$ is a methyl group, and $R_2$ is an isopropyl group when $R_1$ is a phenyl group or a 3-chlorophenyl group.

3. The pesticidal aqueous suspension of claim 1, wherein the particles of said active ingredient being less than about 5 microns in size.

4. The pesticidal aqueous suspension of claim 1, wherein the liquid paraffin has a specific gravity of 0.815 to 0.910 at 25° C. and a viscosity of 50 to 355 Saybolt sec./100° F.

5. The pesticidal aqueous suspension of claim 1, wherein the pesticidally active ingredient is 3-methylphenyl N-methylcarbamate.

6. The pesticidal aqueous suspension of claim 1, wherein the pesticidally active ingredient is 3,4-dimethylphenyl N-methylcarbamate.

7. The pesticidal aqueous suspension of claim 1, wherein the pesticidally active ingredient is 1-naphthyl N-methylcarbamate.

8. A method of killing insects which comprises contacting insects with the pesticidal aqueous suspension according to claim 1, in a pesticidally effective amount.

9. A pesticidal aqueous suspension having an excellent dispersion stability which comprises, based on the total weight of the suspension:
(a) as a pesticidally active ingredient, about 10 to 50 wt% of an N-methyl- or N-phenylcarbamate which is solid and has a solubility in water of 10 to 10,000 ppm at room temperature suspended in water in a finely divided state, said N-methyl- or N-phenylcarbamate being chosen from those represented by the formula:

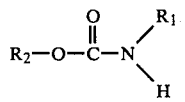

wherein $R_1$ is a methyl group, a phenyl group or a 3-chlorophenyl group; $R_2$ is a 3-methylphenyl group, a 3,4-dimethylphenyl group, a 1-naphthyl group, a 2-methyl-2-(methylthio)propionaldehydooxime group, 2,3-dihydro-2,2-dimethyl-7-benzofuranyl group, a 2-(1-methylethoxy)phenyl group, a 2-chlorophenyl group, a 2-isopropylphenyl group, a 3,5-xylyl group, a 4-dimethylamino-3,5-xylyl group, or a 4-(dimethylamino)-3-methylphenyl group when $R_1$ is a methyl group, and $R_2$ is an isopropyl group when $R_1$ is a phenyl group or a 3-chlorophenyl group;
(b) about 0.5 to 5 wt% of a surfactant having a hydrophile-lipophile balance (HLB) less than 5 selected from the group consisting of sorbitan alkylate, polyoxyethyellene alkyl ester, polyethylene glycol alkyl (or alkylaryl) ether, monoglyceride of fatty acids, propylene glycol alkylate, saccharose alkyl ester and, polyoxyethylene-polyoxypropylene block copolymer;
(c) about 0.5 to 5 wt% of a polyvinyl alcohol having a degree of hydrolysis of about 70 to 90 mol % and a degree of polymerization of about 300 to 2,600;
(d) about 5 to 30 wt% ethylene glycol; and
(e) about 5 to 30 wt% of a liquid paraffin having a specific gravity of 0.815 to 0.910 at 25° C. and a viscosity of 50 to 355 Saybolt sec/100° F.

* * * * *